United States Patent
Lawson

(10) Patent No.: US 9,394,357 B2
(45) Date of Patent: Jul. 19, 2016

(54) METHOD FOR OBTAINING ANTIBODIES

(75) Inventor: Alastair David Griffiths Lawson, Slough (GB)

(73) Assignee: UCB Biopharma SPRL, Brussels (BE)

( * ) Notice: Subject to any disclaimer, the term of this patent is extended or adjusted under 35 U.S.C. 154(b) by 1948 days.

(21) Appl. No.: 11/910,612

(22) PCT Filed: Apr. 4, 2006

(86) PCT No.: PCT/GB2006/001238
§ 371 (c)(1),
(2), (4) Date: Oct. 27, 2008

(87) PCT Pub. No.: WO2006/106323
PCT Pub. Date: Oct. 12, 2006

(65) Prior Publication Data
US 2009/0075398 A1    Mar. 19, 2009

(30) Foreign Application Priority Data
Apr. 5, 2005 (GB) .................................. 0506912.5

(51) Int. Cl.
*C07K 16/00* (2006.01)

(52) U.S. Cl.
CPC .............. *C07K 16/00* (2013.01); *C07K 2317/56* (2013.01); *C07K 2317/565* (2013.01); *C07K 2317/92* (2013.01)

(58) Field of Classification Search
CPC ............... C07K 16/00; C07K 2317/92; C07K 2317/565; C07K 2317/56
USPC ....................................... 436/547; 530/387.3
See application file for complete search history.

(56) References Cited

U.S. PATENT DOCUMENTS

2003/0187247 A1   10/2003 Burton et al.

OTHER PUBLICATIONS

Marks et al. (J.Molec. Biol. 222:581-597 (1991); Abstract).*
Clackson, Tim et al., "Making Antibody Fragments Using Phage Display Libraries", Nature, vol. 352, Aug. 15, 1991, pp. 624-628.
Vaughan, Tristan J. et al., "Human Antibodies with Sub-Nanomolar Affinities Isolated from a Large Non-Immunized Phage Display Library", Nature Biotechnology, vol. 14, Mar. 1996, pp. 309-314.
Marks, James D. et al., "By-Passing Immunization: Building High Affinity Human Antibodies by Chain Shuffling", Bio/Technology, vol. 10, Jul. 1992, pp. 779-783.
Marks, James D., "Antibody Affinity Maturation by Chain Shuffling", Methods in Molecular Biology, vol. 248, 2004, pp. 327-343.
Thompson, Julia et al., "Affinity Maturation of a High-Affinity Human Monoclonal Antibody Against the Third Hypervariable Loop of Human Immunodeficiency Virus: Use of Phage Display to Improve Affinity and Broaden Strain Reactivity", J. Mol. Biol., vol. 256, 1996, pp. 77-88.
Kang, Angray S. et al., "Antibody Redesign by Chain Shuffling from Random Combinatorial Immunoglobulin Libraries", Proc. Natl. Acad. Sci., vol. 88, Dec. 1991, pp. 11120-11123.
Suzuki Motohiro et al, Light chain determines the binding property of human anti-dsDNA IgG autoantibodies, Biochemical and Biophysical Research Communications, Apr. 29, 2000, pp. 240-243, vol. 271, No. 1.
Schier, R et al, Isolation of High-Affinity Monomeric Human Anti-C-ERBB-2 Single Chain FV Using Affinity-Driven Selection, Journal of Molecular Biology, 1996, pp. 28-43, vol. 255, ISSN: 0022-2836, London.
Suzuki M et al, Cloning and functional analysis of anti-double strand DNA IgG autoantibodies using the phage-display method, International Journal of Molecular Medicine, Apr. 1999, pp. 385-390, vol. 3, No. 4, ISSN: 1107-3756.
Aburatani, et al, "Importance of a CDR H3 Basal Residue in VH/VI Interaction of Human Antibodies," 2002, J. Biochem. 132, 775-782.
Ihle, et al, "Cloning, Sequencing and Expression of Immunoglobulin Variable Regions of Murine Monoclonal Antibodies Specific for the P1.7 and P1.16 PorA Protein Loops of Neisseria meningitidis," 2003, Blackwell Publishing Ltd., Scandinavian Journal of Immunology, 57, 453-462.

* cited by examiner

Primary Examiner — Lynn Bristol
(74) Attorney, Agent, or Firm — McDonnell Boehnen Hulbert & Berghoff LLP

(57) ABSTRACT

A method of obtaining at least one recombinant antibody with improved affinity for a selected antigen from a family of antibodies which bind the selected antigen comprising: a) obtaining a family of two or more antibodies which bind the same antigen in which the VH CDR3 amino acid sequence of each antibody in the family is the same length and greater than 60% identical at the amino acid level; b) re-pairing the VH region of an antibody obtained in step (a) with the VL region from a different antibody obtained in step (a) to produce a new recombinant antibody; and c) screening the recombinant antibody produced in step (b) and selecting said antibody if it has improved affinity for the selected antigen compared to any one of the antibodies obtained in step (a).

21 Claims, 2 Drawing Sheets

METHOD FOR OBTAINING ANTIBODIES

Figure 1:
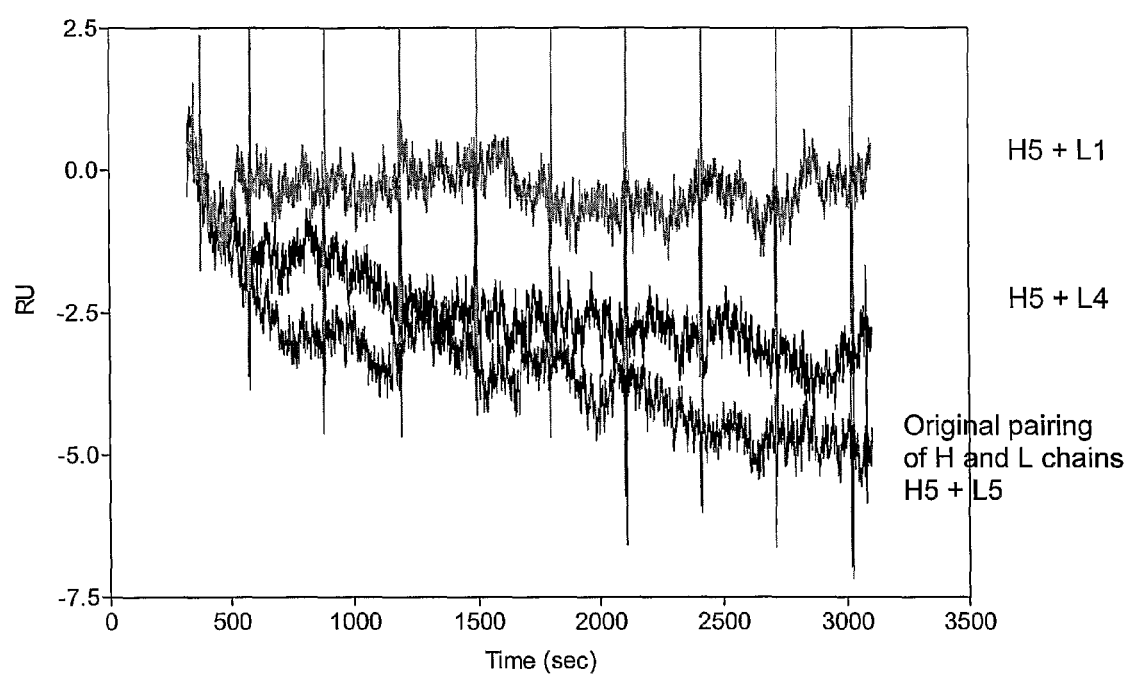

This is a National Stage of International Application No. PCT/GB2006/001238, filed Apr. 4, 2006.

The present invention relates to high affinity antibodies and methods of producing them. In particular, the present invention provides a new method of improving the affinity of antibodies.

The high specificity and affinity of antibodies make them ideal diagnostic and therapeutic agents, particularly for modulating protein:protein interactions. Whole antibodies and antibody fragments are proving to be versatile therapeutic agents, as seen by the recent success of products such as ReoPro®, Remicade™ and Humira®. "ReoPro" is a trademark of Eli Lilly and Company. "Remicade" is a trademark of Centocor Ortho Biotech Inc. "Humira" is a trademark of Abbott Biotechnology Ltd.

Immunoglobulins are Y-shaped molecules comprising two identical heavy chains and two identical light chains. Disulfide bonds link together the heavy and light chain pairs as well as the two heavy chains. Each chain consists of one variable domain that varies in sequence and is responsible for antigen binding, these are known as the $V_H$ and $V_L$ domains for the heavy and light chains respectively. Each chain also consists of at least one constant domain which binds effector molecules. In the light chain there is a single constant domain ($C_L$) and in the heavy chain there are three ($C_H1$, $C_H2$ and $C_H3$).

There are three regions within the variable domains that are hypervariable in sequence set within four more highly conserved framework regions. These hypervariable regions are primarily responsible for antigen recognition and are referred to as 'complementarity-determining regions' (CDRs).

There are many different types of antibodies and fragments thereof that may be used in therapy including whole antibodies and fragments such as Fab, Fab', $F(ab')_2$ and scFv. All of these comprise a pair of $V_H$ and $V_L$ domains which are responsible for antigen binding.

Antibodies for use in therapy are derived from a number of sources including for example immunised animals and phage display libraries. Often the affinity of these antibodies when first isolated is not sufficiently high for direct use in therapy and a number of methods for increasing the affinity of antibodies (affinity maturation) have been developed, including mutating the CDRs (Yang et al., J. Mol. Biol., 254, 392-403, 1995), use of mutator strains of *E. coli* (Low et al., J. Mol. Biol., 250, 359-368, 1996), DNA shuffling (Patten et al., Curr. Opin. Biotechnol., 8, 724-733, 1997) and sexual PCR (Crameri et al., Nature, 391, 288-291, 1998). One particular affinity maturation method is known as 'chain shuffling' in which one antibody chain remains fixed while the other is varied e.g. the $V_H$ domain of a starting antibody is shuffled with a range of other $V_L$ domains and the new $V_H$ and $V_L$ combinations screened to identify those with improved affinity over the starting antibody.

The 'replacement' VH or VL domains used in chain shuffling are typically obtained from libraries of antibody VH or VL region genes constructed from for example, the mRNA of peripheral blood lymphocytes of immunised or unimmunised donors (Clackson et al., 1991, Nature, 352, 624-628; Vaughan et al., 1996, Nature Biotechnology, 14, 309-314). Phage display has typically been used to shuffle antibody sequences as it is possible for phage to accommodate the large library sizes needed to represent all the possible VH or VL genes. Typically the libraries of VH or VL genes are cloned into a vector encoding the complementary VH or VL gene from the starting antibody, see for example Marks et al., 1992, Bio/Technology, 10, 779-783; Marks J D, 2004, Methods in Molecular Biology, 248, 327-343. The various new VH and VL combinations are then expressed as scFvs on the surface of phage and screened for improved affinity. If required, the process can be repeated this time replacing the opposite chain.

In some cases it is still necessary to combine shuffling with other maturation methods, such as CDR mutagenesis in order to produce a high affinity antibody (Thompson et al., J. Mol. Biol., 256, 77-88, 1996).

Shuffling has also been used to investigate the promiscuity of antibody heavy and light chain pairings (Kang et al., 1991, Proc. Natl. Acad. Sci, 88, 11120-11123). Antibodies which bound the hapten, NPN were obtained from phage display libraries derived from an immunised mouse and clonal families of antibody sequences were identified based on sequence similarities and the length of the CDR3 regions of both the heavy and light chains, presumed to be derived from the same initial B cell clone. In each family the CDR3 was the same length. The heavy and light chains from all the antibody families were shuffled and the sequences of the antibodies which still bound the hapten were determined and compared to the starting antibody sequences to determine from which families they were derived. Both incestuous and extraclonal promiscuity of VH and VL chains was observed such that heavy chain variable regions were observed to pair with light chains from both outside and within the complementary light chain family. No affinities were determined for these shuffled clones.

Surprisingly we have now been able to demonstrate that it is possible to produce high affinity antibodies by re-pairing the antibody variable regions within a family of antibodies which bind the same antigen. Surprisingly, the affinity of already high affinity antibodies can be further improved by re-pairing the variable regions between related antibody family members, avoiding the need for large libraries of diverse VH and VL sequences. Despite only small differences in the sequences of the antibodies, large increases in the affinity of these antibodies can be obtained. The frequency of affinity improvement observed is surprising for such a small number of possible combinations of sequences.

Hence the present invention provides a method of obtaining at least one recombinant antibody with improved affinity for a selected antigen from a family of antibodies which bind the selected antigen comprising:
  a) obtaining a family of two or more antibodies which bind the same antigen in which the VH CDR3 amino acid sequence of each antibody in the family is the same length and greater than 60% identical at the amino acid level;
  b) re-pairing the VH region of an antibody obtained in step (a) with the VL region from a different antibody obtained in step (a) to produce a new recombinant antibody; and
  c) screening the recombinant antibody produced in step (b) and selecting said antibody if it has improved affinity for the selected antigen compared to any one of the antibodies obtained in step (a).

The term 'affinity' as used herein refers to the strength with which the antibody binds to the selected antigen. High affinity antibodies have a low dissociation rate constant. The binding affinity of an antibody to an antigen and the dissociation rate of an antibody-antigen interaction can be determined by using methods well known in the art such as BIAcore™ analysis or competitive binding assays. "BIAcore" is a trademark of GE Healthcare Bio-Sciences AB. One example of a competitive binding assay is a radioimmunoassay comprising the incubation of radio-labelled antigen (e.g. .sup.3H or .sup.125I) with the antibody of interest in the presence of increasing amounts of unlabelled antigen, and the detection of the antibody bound to the labelled antigen. The affinity of the antibody of interest for a particular antigen and the binding off-rates can be determined from the data by Scatchard plot analysis. Preferably BIAcore™ is used to determine the affinity of the antibodies of the present invention. BIAcore™ is an automated biosensor system that can be used to measure molecular interactions (Karlsson, et al., 1991, J. Inmunol. Methods, 145, 229-240). In this method, the concentration of antigen does not in many cases need to be accurately determined, and it is possible to obtain dissociation-rate measurements for already high affinity antibodies.

Preferably the antibodies obtained in step (a) of the method have a high affinity for the selected antigen. By high affinity we mean preferably in the nanomolar range, more preferably in the picomolar range. Preferably the antibodies obtained in step (a) of the method have an affinity for the selected antigen in the range of 1 pM to 10 nM, more preferably in the range 5 pM to 500 pM, even more preferably 10 pM to 200 pM. In one embodiment the antibodies obtained in step (a) have an affinity for the selected antigen of 10 to 100 pM.

The term 'antibody' as used herein includes whole antibodies and functionally active fragments or derivatives thereof and may be, but are not limited to monoclonal, humanized or chimeric antibodies, single chain antibodies, Fab fragments, Fab' and F(ab')$_2$ fragments and epitope-binding fragments of any of the above.

Antibodies therefore include immunoglobulin molecules and immunologically active portions of immunoglobulin molecules, i.e. molecules that contain an antigen-binding site that specifically binds an antigen. The immunoglobulin molecules of the invention can be of any class (e.g. IgG, IgE, IgM, IgD or IgA) or subclass of immunoglobulin molecule.

Humanized antibodies are antibody molecules from non-human species having one or more complementarity determining regions (CDRs) from the non-human species and a framework region from a human immunoglobulin molecule (see, for example, U.S. Pat. No. 5,585,089).

Chimeric antibodies are those antibodies encoded by immunoglobulin genes that have been genetically engineered so that the light and heavy chain genes are composed of immunoglobulin gene segments belonging to different species. These chimeric antibodies are likely to be less antigenic than the original starting antibody.

The residues in antibody variable domains are conventionally numbered according to a system devised by Kabat et al. This system is set forth in Kabat et al., 1987, in Sequences of Proteins of Immunological Interest, US Department of Health and Human Services, NIH, USA. This numbering system is used in the present specification except where otherwise indicated.

The Kabat residue designations do not always correspond directly with the linear numbering of the amino acid residues. The actual linear amino acid sequence may contain fewer or additional amino acids than in the strict Kabat numbering corresponding to a shortening of, or insertion into, a structural component, whether framework or CDR, of the basic variable domain structure. The correct Kabat numbering of residues may be determined for a given antibody by alignment of residues of homology in the sequence of the antibody with a "standard" Kabat numbered sequence.

The term 'antigen' as used herein refers to any known or unknown substance that can be recognised by an antibody, including proteins, glycoproteins and carbohydrates. Preferably, these antigens include biologically active proteins, such as hormones, cytokines and their cell surface receptors, bacterial or parasitic cell membranes or purified components thereof, and viral antigens. The antigen may be any cell-associated antigen, for example a cell surface antigen on cells such as bacterial cells, yeast cells, T-cells, endothelial cells or tumour cells, or it may be a soluble antigen. Antigens may also be any medically relevant antigen such as those antigens upregulated during disease or infection, for example receptors and/or their corresponding ligands. Particular examples of cell surface antigens include adhesion molecules, for example integrins such as β1 integrins e.g. VLA-4, E-selectin, P selectin or L-selectin, CD2, CD3, CD4, CD5, CD7, CD8, CD11a, CD11b, CD18, CD19, CD20, CD23, CD25, CD33, CD38, CD40, CD45, CDW52, CD69, CD70, CD134, carcinoembryonic antigen (CEA), MUC-1, MHC Class I and MHC Class II antigens, and VEGF, and where appropriate, receptors thereof. Soluble antigens include interleukins such as IL-1, IL-2, IL-3, IL-4, IL-5, IL-6, IL-8, IL-12, IL-16 or IL-17, viral antigens for example respiratory syncytial virus or cytomegalovirus antigens, immunoglobulins, such as IgE, interferons such as interferon α, interferon β or interferon γ, tumour necrosis factor-α, tumor necrosis factor-β, colony stimulating factors such as G-CSF or GM-CSF, and platelet derived growth factors such as PDGF-α, and PDGF-β and where appropriate receptors thereof.

In one example, the antigen for use in the present invention is available in a pure form obtained either by direct purification from the native source or by recombinant expression and purification of said antigen.

In another example, the antigen may be expressed on the surface of a cell, either naturally or recombinantly. Such cells may include but are not limited to mammalian cells, immunomodulatory cells, lymphocytes, monocytes, polymorphs, T cells, tumour cells, yeast cells, bacterial cells, infectious agents, parasites, plant cells, and transfected cells such as NSO, CHO, COS and 293 cells.

In another example, the antigen is unknown and the antigen is any material that would provide a source of possible antigens. Examples of suitable materials include those of animal, mammalian, plant, yeast, bacterial or viral origin. The material may be a cell or a population of cells for which it would be desirable to isolate antibodies to, such as mammalian cells, immunomodulatory cells, lymphocytes, monocytes, polymorphs, T cells, tumour cells, yeast cells, bacterial cells, infectious agents, parasites and plant cells. In one embodiment, the cell is a tumour cell.

In step (a) of the method of the present invention a family of two or more antibodies which bind the same antigen are obtained. The antibodies may be obtained by any suitable method known in the art, including for example phage display and in vivo immune responses. The antibodies obtained in step (a) which bind the same antigen may also have one or more functional characteristics in common e.g. neutralisation of a biological activity or binding to a particular epitope. These may be identified using one or more functional assays as described herein below. In one example the antibodies obtained in step (a) are obtained via phage display. Various phage display methods are known in the art see for example Brinkman et al. (in J. Immunol. Methods, 1995, 182: 41-50), Ames et al. (J. Immunol. Methods, 1995, 184:177-186), Kettleborough et al. (Eur. J. Immunol. 1994, 24:952-958), Persic et al. (Gene, 1997 187 9-18), Burton et al. (Advances in Immunology, 1994, 57:191-280) and WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108.

Preferably the antibodies obtained in step (a) are derived from an in vivo generated immune response. Accordingly, in one embodiment, in step (a) of the method of the present invention a family of two or more in vivo generated antibodies is obtained from at least one animal which has generated an in vivo immune response to a selected antigen. Preferably the antibodies obtained all bind to the same selected antigen and retain the in vivo generated VH and VL pairings.

Hence in one embodiment the present invention provides a method of obtaining at least one recombinant antibody with improved affinity for a selected antigen from a family of in vivo generated antibodies which bind the selected antigen comprising:
 a) obtaining a family of two or more in vivo generated antibodies which bind the same antigen and retain the in vivo generated VH and VL pairings in which the VH CDR3 amino acid sequence of each antibody in the family is the same length and greater than 60% identical at the amino acid level;
 b) re-pairing the VH region of an antibody obtained in step (a) with the VL region from a different antibody obtained in step (a) to produce a new recombinant antibody; and
 c) screening the recombinant antibody produced in step (b) and selecting said antibody if it has improved affinity for the selected antigen compared to any one of the antibodies obtained in step (a).

Typically the antibodies for use in step (a) are obtained using any suitable method well known in the art for obtaining antibodies from in vivo generated immune responses.

In one example the antibodies obtained in step (a) are monoclonal antibodies. Monoclonal antibodies may be prepared by any method known in the art such as the hybridoma technique (Kohler & Milstein, *Nature,* 1975, 256, 495-497), the trioma technique, the human B-cell hybridoma technique (Kozbor et al., *Immunology Today,* 1983, 4, 72) and the EBV-hybridoma technique (Cole et al., "Monoclonal Antibodies and Cancer Therapy", pp. 77-96, Alan R. Liss, Inc., 1985).

In another example the antibodies are obtained in step (a) using methods such as those described in Babcook, J. et al., *Proc. Natl. Acad. Sci. USA,* 1996, 93 (15), 7843-7848, WO 92/02551, WO2004/051268 and WO2004/106377.

Antibodies may be obtained from one or more animals of the same species.

The animal may be one that has been immunized with an antigen and has preferably not previously been exposed to the antigen of interest (or an animal which is not known to have been exposed to the antigen of interest or which is not believed to have been exposed to the antigen of interest). Alternatively or in addition, the animal or human may be one which has developed an immune response to an antigen as a result of disease.

Where appropriate, animals may be immunized with a selected antigen using any of the techniques well known in the art suitable for generating an immune response (see Handbook of Experimental Immunology, D. M. Weir (ed.), Vol 4, Blackwell Scientific Publishers, Oxford, England, 1986). Many warm-blooded animals, such as rabbits, mice, rats, sheep, cows, chickens or pigs may be immunized in order to obtain antibodies. However, mice, rabbits, pigs and rats are generally preferred. High numbers of antibody producing cells can be found in the peripheral spleen and lymph node of the immunised animal and once an immune response has been generated and the animal has been sacrificed, the spleen and lymph nodes are removed.

Alternatively antibodies can also be obtained from an animal that has generated the antibodies during the course of a disease, in particular a human. For instance, antibody producing cells e.g. B cells, from a human with a disease of unknown cause, such as cancer, may be obtained and used to assist in the identification of antibodies which have an effect on the disease process or which may lead to identification of an agent or body component that is involved in the cause of the disease. Similarly, antibodies may be obtained from subjects with disease of known cause such as malaria. These antibody producing cells may be derived from the blood or lymph nodes, as well as from other diseased or normal tissues.

Antibodies may be obtained from the antibody producing cells generated by the immune response by any method known in the art including the methods described herein above for the isolation of monoclonal antibodies. Preferably however, antibodies for use as the starting population in step (a) of the method of the present invention are obtained by isolating individual B-cells which produce antigen specific antibodies. The term "B cell" as used herein includes any B cell or derivative thereof producing an antibody, such as a B-lymphocyte, a plasma cell, a plasmablast, an activated B cell or a memory B cell. These cells may secrete antibodies and/or maintain antibodies on the surface of the cell.

A population of antibody producing cells may be enriched by methods based upon the size or density of the antibody producing cells relative to other cells. An example of the use of Percoll to separate cells according to density is described by van Mourik and W. P. Zeizlmaker in Methods in Enzymology 121; 174-182 (J. J. Langone, H. H. van Vunakis (eds.), Academic Press Inc., New York). Gradients of varying density of solutions of bovine serum albumin can also be used to separate cells according to density. (See N. Moav and T. N. Harris, J. Immunol. 105, 1512, 1970; see also Raid, D. J. in Selected Methods in Cellular Immunology, B. Misheli and S. Shiigi (eds.), W. H. Freeman and Co., San Francisco, 1987). Preferably separation is achieved by centrifugation with Ficoll-Hypaque (Pharmacia, Uppsala, Sweden).

In one particular embodiment antibody producing cells once obtained e.g. by Ficoll separation are cultured in 96 well microtitre plates in T cell conditioned media (3%) and EL-4 cells ($5 \times 10^4$/well) for between around seven and around fourteen days optionally at a cell density that statistically provides that any antibodies which bind the selected antigen will be present as single clones. Following culturing, the supernatants containing secreted antibody are screened for antigen binding by, for example, FMAT, FACS, ELISA or BIAcore™, and optionally further screened for affinity and/or a functional characteristic in functional assays such as detection of receptor signalling through antibody binding (agonism) or blocking of receptor signalling through antibody binding to the receptor or the ligand (neutralisation/antagonism) or apoptosis.

Other suitable assays for use in selecting antibodies for use in step (a) of the method include assays to identify antibodies which bind to a particular region or epitope of an antigen, for example to identify cross-blocking antibodies. These can be identified using any suitable method in the art, for example by using competition ELISA or BIAcore™ where binding of the cross blocking antibody to a selected antigen prevents the binding of an antibody already known to bind that antigen or vice versa. Preferably two or more assays are used to screen the antibodies, in particular an assay for antigen binding is followed by one or more functional assays or vice versa. Hence in one example the antibodies obtained in step (a) bind the same antigen and have one or more functional characteristics in common.

Methods for identifying B cells producing antibodies which bind the selected antigen from a population of B cells, either directly from the animal or following culturing and pre-screening using the methods described above have been described in Babcook, J. et al., *Proc. Natl. Acad. Sci. USA*, 1996, 93 (15), 7843-7848, WO 92/02551, WO2004/051268, WO2004/106377, WO2005/019823 and WO2005/019824. Hence in one preferred embodiment the antibodies obtained in step (a) of the method are obtained from individual isolated B-cells preferably isolated using the homogeneous fluorescence assays described in WO2004/051268.

Once the antibodies have been obtained, for example once individual B cells have been identified and/or monoclonal antibodies have been produced, the sequences encoding the variable regions of these antibodies can be obtained. The variable region sequences can for example be obtained by first sequencing the antibody protein produced by the hybridoma, B-cell or phage and determining the encoding nucleic acid sequence. More preferably the immunoglobulin variable region (VH and VL) DNA or cDNA may be sequenced instead. Where the antibody is derived from a hybridoma cell line or isolated B-cell the cDNAs encoding the variable regions may be amplified using PCR by for example the methods described in Babcook, J. et al., *Proc. Natl. Acad. Sci. USA*, 1996, 93(15), 7843-7848, and in WO 92/02551.

The variable region VH and VL regions are well known in the art for example, in human IgG subgroup 1 VH and VL can be found at residues 1-113 and 1-109 respectively.

Optionally, once the VH and VL gene sequences have been obtained they can be expressed in recombinant cell lines to produce whole antibodies or fragments thereof using any suitable method, whilst retaining the original, for example, in vivo generated, VH and VL pairings (Verma et al., 1998, *Journal of Immunological Methods*, 216, 165-181; Simmons et al., Journal of Immunological Methods, 2002, 263, 133-147; Babcook et al, supra and WO92/02551). Once the antibodies have been expressed, they may be screened for antigen binding, affinity and functional characteristics. These screens may be performed for the first time if the antibodies were not screened previously, for example before the B cells were isolated. Alternatively the screens may be used to confirm the properties of the isolated antibody or to farther characterise the antibody.

Once the variable region sequences have been obtained from at least two antibodies which bind the same selected antigen it is possible to group the sequences into families of sequences for use in step (a) of the method. A family of antibodies is defined in the present invention as a collection of two or more antibodies having the following characteristics in common:
  1) bind the same selected antigen
  2) the length of the VH CDR3 amino acid sequence is the same
  3) the VH CDR3 sequences are greater than 60% identical at the amino acid level.

In one embodiment a family of antibodies is defined in the present invention as a collection of two or more in vivo generated antibodies which retain the natural in vivo generated VH and VL pairings having the following characteristics in common:
  1) bind the same selected antigen
  2) the length of the VH CDR3 amino acid sequence is the same
  3) the VH CDR3 sequences are greater than 60% identical at the amino acid level.

CDR3 of the heavy chain variable domain (VH CDR3) is located at residues 95-102 according to the Kabat numbering system.

The length of the VH CDR3 amino acid sequence in the antibody families of the present invention is the same.

The VH CDR3 sequences in the family are typically greater than 60% identical at the amino acid level. In one embodiment the VH CDR3 sequences are greater than 70% identical, in another embodiment the VH CDR3 sequences are greater than 80% identical, in another embodiment the VH CDR3 sequences are greater than 90% identical, in another embodiment the VH CDR3 sequences are greater than 95% identical, in another embodiment the VH CDR3 sequences are greater than 96% identical, in another embodiment the VH CDR3 sequences are greater than 97% identical, in another embodiment the VH CDR3 sequences are greater than 98% identical, in another embodiment the VH CDR3 sequences are greater than 99% identical and in another embodiment the VH CDR3 sequences are 100% identical.

The term "Identity", as used herein, is calculated for any particular region of the antibody sequence (e.g. VH CDR3) as $(1-(A/B))*100$, wherein A is the total number of positions in the aligned sequences at which at least one member of the family of antibodies differs from any other member in the family and B is the total number of residues in that region of sequence. For example, for calculating the identity of the VH CDR3 regions, B is the total number of amino acids in the VH CDR3 and A is the total number of amino acid positions in the family of aligned VH CDR3 sequences at which at least one member of the family of antibodies differs from any other member in the family.

The overall similarity of the entire VH and VL sequences may vary, in particular depending on the number of family members. Where there are a large number of antibodies in the family the overall sequence similarity of the VH and VL sequences will be lower than where there are fewer family members. This is a desirable feature of the invention whereby higher affinity antibodies can be obtained by utilising this diversity.

Typically the VH sequences in a family are greater than 50% identical, greater than 60% identical, greater than 70% identical or greater than 80% identical depending on the number of sequences in the family as set out above.

Similarly the VL sequences in a family may be greater than 50% identical, greater than 60% identical, greater than 70% identical or greater than 80% identical.

In one example of the present invention therefore the family of antibodies obtained in step (a) is further characterised in that the VH sequences are greater than 60% identical and the VL sequences are greater than 60% identical.

Hence in one embodiment of the present invention a family of antibodies is defined as two or more antibodies which all have the following characteristics in common:
  1) bind the same selected antigen
  2) the length of the VH CDR3 amino acid sequence is the same
  3) the VH CDR3 sequences are greater than 60% identical at the amino acid level.
  4) the VH sequences are greater than 60% identical at the amino acid level
  5) the VL sequences are greater than 60% identical at the amino acid level In one embodiment of the present invention a family of antibodies is defined as two or more in vivo generated antibodies which retain the in vivo generated VH and VL pairings which all have the following characteristics in common:
  1) bind the same selected antigen
  2) the length of the VH CDR3 amino acid sequence is the same 3) the VH CDR3 sequences are greater than 60% identical at the amino acid level.
4) the VH sequences are greater than 60% identical at the amino acid level
5) the VL sequences are greater than 60% identical at the amino acid level The family of antibodies obtained in step (a) comprises at least 2 antibodies. In one embodiment the family of antibodies obtained in step (a) comprises three or more antibodies. In one embodiment the family of antibodies obtained in step (a) comprises 4 or more antibodies. In one embodiment the family of antibodies obtained in step (a) comprises 5 or more antibodies. In a further embodiment the family of antibodies obtained in step (a) comprises 6 or more antibodies.

Typically the family of antibodies obtained in step (a) comprises between 2 and 100 antibodies. In one embodiment the family of antibodies obtained in step (a) comprises between 2 and 50 antibodies. In another embodiment the family of antibodies obtained in step (a) comprises between 2 and 40 antibodies. In another embodiment the family of antibodies obtained in step (a) comprises between 2 and 30 antibodies. In another embodiment the family of antibodies obtained in step (a) comprises between 2 and 20 antibodies. In one embodiment the family of antibodies obtained in step (a) comprises between 2 and 10 antibodies.

In one example, described herein, six antibody family members are obtained in step (a) of the method which have identical VH CDR3 amino acid sequences and both the VH and VL regions are greater than 80% identical.

Where no two antibodies which bind a selected antigen obtained using the methods described herein above share these sequence properties, further antibodies can be isolated and screened using the methods described above to obtain additional family members.

Once a family of at least two antibodies comprising VH and VL regions has been obtained in step (a) of the method, a VH region of one of the antibodies in the family is re-paired with a VL region from a different antibody in the family in step (b) of the method, to produce at least one new VH and VL pair. Hence in step (b) of the method the VH region of an antibody obtained in step (a) of the method is re-paired with the VL region from a different antibody obtained in step (a) to produce a new recombinant antibody. Preferably at least two different VH:VL pairs are produced, more preferably all possible combinations of VH and VL pairs are produced. For example, if there are six antibodies in the family and hence six pairs of VH and VL genes there will be 36 possible combinations of VH and VL pairs to be tested of which 30 will be new combinations. Hence in one embodiment in step (b) each VH region from the antibodies obtained in step (a) is re-paired with each VL region such that every new VH:VL combination is produced as a recombinant antibody and at least one of the recombinant antibodies produced is screened in step (c). Preferably every new VH:VL combination produced in step (b) is screened in step (c).

Any suitable method known in the art may be used to re-pair the VH and VL regions in step (b) of the method. Preferably in the method of the present invention the VH and VL genes are re-paired by incorporating each individual VH and VL gene into a different vector and combinations of VH and VL pairs created by co-expressing one VH and one VL containing vector in a host cell such that a functional VH and VL pair is produced in any suitable antibody format.

General methods by which the vectors may be constructed, transfection methods and culture methods are well known to those skilled in the art. In this respect, reference is made to "Current Protocols in Molecular Biology", 1999, F. M. Ausubel (ed), Wiley Interscience, New York and the Maniatis Manual produced by Cold Spring Harbor Publishing. Any suitable host cell/vector system may be used for expression of the DNA sequences encoding the antibody molecules. Bacterial, for example *E. coli*, and other microbial systems may be used or eukaryotic, for example mammalian, host cell expression systems may also be used. Suitable mammalian host cells include CHO and NSO. The methods for expressing these antibodies are well known in the art (see for example, Verma et al., 1998, *Journal of Immunological Methods,* 216, 165-181; Simmons et al., Journal of Immunological Methods, 2002, 263, 133-147).

In one example the appropriate vectors contain heavy and light chain constant regions or parts thereof such that whole antibodies or antibody fragments such as Fab or Fab' may be produced. With each VL and VH in separate vectors it is possible to readily co-transfect each VH and VL combination into a suitable host cell, for example CHO cells. For example, the V-region may be sub-cloned into the expression vectors pMRR10 and pMRR14 (see for example WO2004/072116). These are separate vectors for expression of the light and heavy chain respectively and contain genomic DNA encoding constant region genes for human kappa light chain and gamma-4 heavy chain respectively. These vectors may then be co-transfected into CHO cells and a whole antibodies produced by culturing the CHO cells.

Alternatively, but less conveniently, each VH and VL pair may be expressed in the same vector either as whole antibodies or as fragments, including scFv.

Following expression of the re-paired VH and VL sequences, the antibodies which may be optionally purified, are screened in step (c) of the method to identify those antibodies with improved affinity over the starting population of antibodies obtained in step (a) of the method.

Optionally, in step (c) the binding of the antibodies to the selected antigen may be determined before the affinity of those antibodies which bind the selected antigen is determined; alternatively, antigen binding and affinity can be determined simultaneously. For example, in step (c), ELISA may be used to assay all the antibodies produced in step (b) to determine which antibodies bind the selected antigen and subsequently those antibodies which bind the antigen are screened to identify those with improved affinity over the starting antibody populations. In another example in step (c) antigen binding and affinity are determined simultaneously using for example BIAcore™.

An antibody is selected in step (c) of the method if it has improved affinity for the selected antigen compared to any one of the antibodies obtained in step (a) of the method. One or more antibodies with improved affinity may be selected in step (c). Preferably at least the antibody with the highest affinity for the selected antigen is selected in step (c) of the method. If an antibody with improved affinity is not identified in step (c), steps (b) and (c) of the method may be repeated for different VH:VL pairs until an antibody with improved affinity is identified in step (c).

An increase in affinity can be determined by any of the methods described herein. An increase in affinity also includes a reduction in the off-rate i.e. a reduction in the dissociation rate between the antibody and antigen (Kd) as observed in the examples described herein.

In a preferred embodiment the present invention provides a method of obtaining at least one recombinant antibody with improved affinity for a selected antigen from a family of in vivo generated antibodies which bind the selected antigen comprising:

a) obtaining a family of two or more in vivo generated antibodies which bind the same antigen and retain the in vivo generated VH and VL pairings in which the VH CDR3 amino acid sequence of each antibody in the family is the same length and greater than 70% identical at the amino acid level;
b) re-pairing the VH region from each of the antibodies obtained in step (a) with the VL region from each of the other antibodies such that every new VH:VL combination is produced as an antibody; and
c) screening each antibody produced in step (b) for binding to the selected antigen, determining the binding affinity of any of the antibodies which bind the selected antigen, identifying which of said antibodies has improved affinity for the selected antigen compared to any one of the antibodies provided in step (a) and selecting one or more of said antibodies each of which has improved affinity.

Also provided by the present invention, is at least one high affinity antibody obtained in step (c) of the method of the present invention. Preferably the antibody is an antibody with at least picomolar affinity for the selected antigen. In one embodiment the antibody has an affinity of 100 pM or less for the selected antigen. In one embodiment the antibody has an affinity of 75 pM or less for the selected antigen. In one embodiment the antibody has an affinity of 50 pM or less for the selected antigen. In one embodiment the antibody has an affinity of 25 pM or less for the selected antigen. Preferably the antibody has an affinity of 10 pM or less for the selected antigen, more preferably, 5 pM or less, even more preferably 1 pM or less.

In one embodiment the antibody selected in step (c) of the method has at least a 1.5 fold higher affinity for the selected antigen than any one of the antibodies obtained in step (a). In one embodiment the antibody selected in step (c) of the method has at least a 2 fold higher affinity for the selected antigen than any one of the antibodies obtained in step (a). In one embodiment the antibody selected in step (c) of the method has at least a 5 fold higher affinity for the selected antigen than any one of the antibodies obtained in step (a). In one embodiment the antibody selected in step (c) of the method has at least a 10 fold higher affinity for the selected antigen than any one of the antibodies obtained in step (a). In one embodiment the antibody selected in step (c) of the method has at least a 20 fold higher affinity for the selected antigen than any one of the antibodies obtained in step (a). In one embodiment the antibody selected in step (c) of the method has at least a 50 fold higher affinity for the selected antigen than any one of the antibodies obtained in step (a). In one embodiment the antibody selected in step (c) of the method has at least a 100 fold higher affinity for the selected antigen than any one of the antibodies obtained in step (a).

The antibodies selected in step (c) of the method typically have a lower (slower) dissociation rate than the antibodies obtained in step (a) of the method. In one embodiment the antibody selected in step (c) of the method has a dissociation rate (kd 1/s) which is at least 1.5 fold lower than any one of the antibodies obtained in step (a) of the method. In one embodiment the antibody selected in step (c) of the method has a dissociation rate (kd 1/s) which is at least 2 fold lower than any one of the antibodies obtained in step (a) of the method. In one embodiment the antibody selected in step (c) of the method has a dissociation rate (kd 1/s) which is at least 2.5 fold lower than any one of the antibodies obtained in step (a) of the method. In one embodiment the antibody selected in step (c) of the method has a dissociation rate (kd 1/s) which is at least 3 fold lower than any one of the antibodies obtained in step (a) of the method. In one embodiment the antibody selected in step (c) of the method has a dissociation rate (kd 1/s) which is at least 4 fold lower than any one of the antibodies obtained in step (a) of the method. In one embodiment the antibody selected in step (c) of the method has a dissociation rate (kd 1/s) which is at least 5 fold lower than any one of the antibodies obtained in step (a) of the method.

The antibodies obtained by the method of the present invention may be whole antibodies, humanized or chimeric antibodies, single chain antibodies, Fv fragments, Fab fragments, Fab' and F(ab')$_2$ fragments and epitope-binding fragments of any of the above.

It will be appreciated that the antibody format of the recombinant antibody obtained by the method of the present invention may be altered once it has been selected in step (c) of the method. For example the method may further comprise an additional step (d) in which the antibody selected in step (c) is humanised. Humanized antibodies are typically antibody molecules from non-human species having one or more complementarity determining regions (CDRs) from the non-human species and a framework region from a human immunoglobulin molecule (see, for example, U.S. Pat. No. 5,585,089). It will be appreciated that where the antibody isolated from an in vivo generated immune response is a human antibody this may also be 'humanised' to make the antibody conform to a more frequently occurring framework sequence or to incorporate or remove specific characteristics.

Hence the invention also provides a high affinity humanised antibody obtained in step (d) of the method. Preferably the humanised antibody has a picomolar affinity for the selected antigen. In one embodiment the antibody has an affinity of 100 pM or less. In one embodiment the antibody has an affinity of 75 pM or less. In one embodiment the antibody has an affinity of 50 pM or less. In one embodiment the antibody has an affinity of 25 pM or less. Preferably the antibody has an affinity of 10 pM or less for the selected antigen, more preferably 5 pM or less, even more preferably, 1 pM or less.

The present invention will now be described by way of example only, in which reference is made to:

FIG. 1: Shows dissociation phases of antigen/antibody complexes by BIAcore™. Original pairing of H5 and L5 is compared to new pairings of H5 with L1 and H5 with L4.

Figure 2:
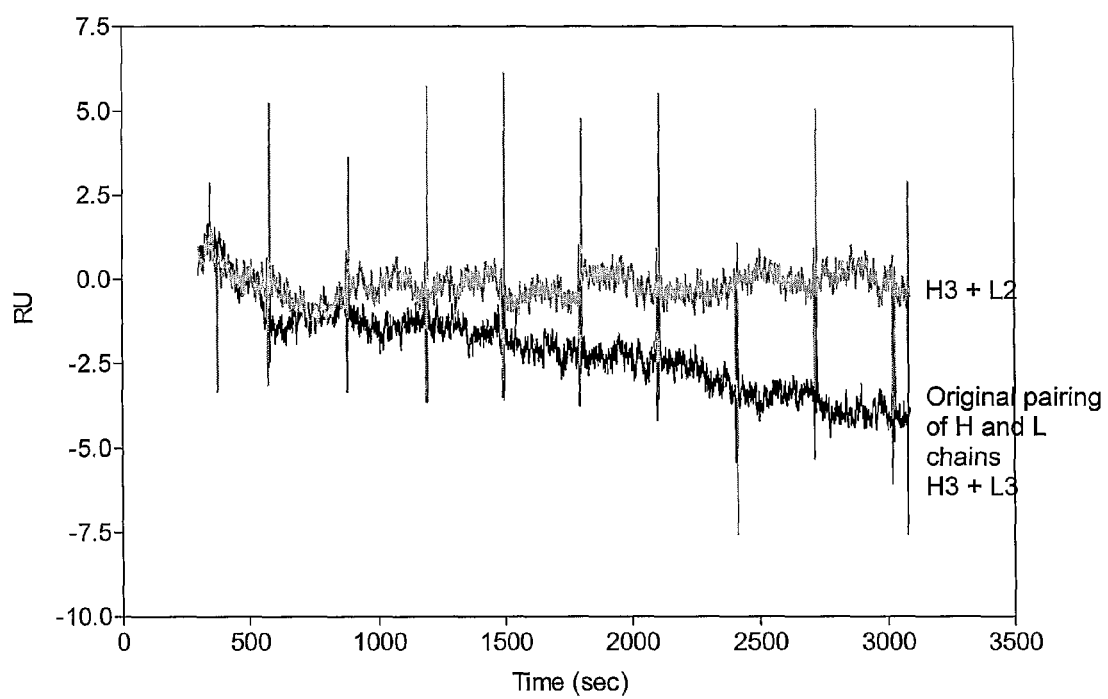

FIG. 2: Shows dissociation phases of antigen/antibody complexes by BIAcore™. Original pairing of H3 and L3 is compared to the new pairing of H3 with L2.

EXAMPLES

Example 1

Antibodies were derived from hyperimmune mice using methods essentially as described in WO92/02551 and using a soluble protein antigen of greater than 15 kDa in size. Following screening of supernatants for binding to antigen individual V region sequence pairs were obtained from isolated single B cells which were detected using the method described in WO2004/051268. The V regions obtained, following sequence analysis, were grouped into families. In one family 6 family members were identified. All six had identical VH CDR3 amino acid sequences and the VH regions were 84% identical and VL regions 88% identical at the amino acid level. The V regions were cloned into mouse constant regions in single gene vectors and transiently expressed in CHO cells in each of the possible heavy and light chain pairs. Eg. H1 and L1, H1 and L2, H1 and L3, H1 and L4, H1 and L5, H1 and L6, H2 and L1, H2 and L2 etc.

All 36 combinations of H and L chains were created and screened of which 30 combinations were new.

Method for Long Off-Rate Measurements for Antibody-Antigen Complexes.

Preparation of Capture Surface.

All experiments were performed on a Biacore™ 3000 biosensor. Goat anti-mouse IgG-Fc (Jackson 115-006-071) coupled to CM5 sensor surface using standard amine coupling chemistry. Coupling level restricted to ~3600 RU. A blank flow cell was also prepared. All data is based on subtracting the signal obtained over the blank flow cell from the signal obtained over the goat anti-mouse IgG-Fc surface.

Off-Rate Determination.

All experiments performed in HBS-EP buffer (10 mM Hepes, pH 7.4, 150 mM NaCl, 3 mM EDTA, 0.005% v/v surfactant P20) containing 1 mg/mL CD-Dextran.

Antibodies were captured to the sensor surface to give ~200 RU of captured material (typically, a 10 µL injection of a 3 µg/mL solution of antibody at 10 µL/min). Antigen was bound to the antibody (3 minute injection of 12.5 nM antigen at 30 µL/min. The flow rate was then increased to 100 µL/min and dissociation of the bound antigen was followed for 45 minutes.

Dissociation of the captured antibody from the anti-mouse IgG-Fc surface was controlled for by performing a dissociation experiment in which buffer was substituted for antigen in the main dissociation experiment. This buffer control data was subtracted from the antigen dissociation data ("double referencing") prior to data analysis.

Data Presentation.

Data is presented by aligning the data for different antibodies from the beginning of the dissociation phase. Visually it is clear which chain combinations/antibodies have the improved (slower) dissociation rate (FIGS. 1 and 2).

This same data can also be fitted to a monophasic model of dissociation and the dissociation rate constant calculated derived from this. This is an automated procedure using the BIAevaluation software (version 3.2).

The data is shown in Table 1:

TABLE 1

Dissociation rate constants for the heavy and light chain pairs.

| Pair | kd (1/s) |
|---|---|
| H3 L3 | 2.73E−05 |
| H3 L2 | 1.07E−05 |
| H5 L5 | 3.63E−05 |
| H5 L4 | 3.32E−05 |
| H5 L1 | 6.18E−06 |

3 new pairs had improved antigen binding over the original pairs.

The invention claimed is:

1. A method of obtaining at least one recombinant antibody with increased affinity for a selected antigen from a family of antibodies which bind the selected antigen comprising:
   a) obtaining from B cells a family of two or more antibodies which bind the same antigen and retain the in vivo generated VH and VL pairings in which the VH CDR3 amino acid sequence of each antibody in the family is 100% identical, wherein the antibodies are obtained by isolating individual B-cells which produce antigen specific antibodies and wherein each antibody obtained in step a) is isolated from a single B cell, and the sequences encoding the variable regions of those antibodies are obtained;
   b) preparing new combinations of VH and VL regions by re-pairing the VH region of an antibody obtained in step a) with the VL region from a different antibody obtained in step (a) to produce new recombinant antibody; and
   c) screening the recombinant antibody produced in step (b) and selecting said antibody if it has increased affinity for the selected antigen compared to any one of the antibodies obtained in step (a).

2. The method according to claim 1 in which the family of two or more antibodies obtained in step (a) are further characterized in that the VH region of each antibody is greater than 80% identical at the amino acid level and the VL region of each antibody is greater than 80% identical at the amino acid level.

3. The method according to claim 1 in which in step (b) each VH region from the antibodies obtained in step (a) is re-paired with each VL region such that every new VH:VL combination is produced as a recombinant antibody or fragment thereof and at least one of the recombinant antibodies produced is screened in step (c).

4. The method of claim 3 wherein every new antibody combination produced in step (b) is screened in step (c).

5. The method according to claim 1 in which steps (b) and (c) are repeated for different VH:VL pairs until an antibody with improved affinity is identified in step (c).

6. The method of claim 1 wherein three or more antibodies are obtained in step (a).

7. The method according to claim 1 in which the family of antibodies obtained in step (a) are in vivo generated antibodies which bind the same antigen and retain the in vivo generated VH and VL pairings.

8. The method according to claim 1 further comprising the step (d) in which the antibody obtained in step (c) is humanised.

9. The method according to claim 1 in which the antibody obtained in step (c) of the method has an affinity of 100 pM or less.

10. The method according to claim 2 in which in step (b) each VH region from the antibodies obtained in step (a) is re-paired with each VL region such that every new VH:VL combination is produced as a recombinant antibody or fragment thereof and at least one of the recombinant antibodies produced is screened in step (c).

11. The method according to claim 2 in which steps (b) and (c) are repeated for different VH:VL pairs until an antibody with improved affinity is identified in step (c).

12. A method of obtaining at least one recombinant antibody with increased affinity for a selected antigen from a family of antibodies which bind the selected antigen comprising:
   (a) obtaining from B cells a family of two or more antibodies which bind the same antigen and retain the in vivo generated VH and VL pairings in which the VH CDR3 amino acid sequence of each antibody in the family is 100% identical;
   (b) re-pairing the VH region of an antibody obtained in step (a) with the VL region from a different antibody obtained in step (a) to produce a new recombinant antibody; and
   (c) screening the recombinant antibody produced in step (b) and selecting said antibody if it has increased affinity for the selected antigen compared to any one of the antibodies obtained in step (a), wherein in step (a) the antibodies are obtained by isolating individual B-cells which produce antigen specific antibodies and the sequences encoding the variable regions of those antibodies are obtained, and wherein the family of antibodies obtained in step (a) are in vivo generated antibodies which bind the same antigen and retain the in vivo generated VH and VL pairings.

13. The method according to claim 12 in which the family of two or more antibodies obtained in step (a) are further characterized in that the VH region of each antibody is greater than 80% identical at the amino acid level and the VL region of each antibody is greater than 80% identical at the amino acid level.

14. The method according to claim 12 in which in step (b) each VH region from the antibodies obtained in step (a) is re-paired with each VL region such that every new VH:VL combination is produced as a recombinant antibody or fragment thereof and at least one of the recombinant antibodies produced is screened in step (c).

15. The method of claim 14 wherein every new antibody combination produced in step (b) is screened in step (c).

16. The method according to claim 12 in which steps (b) and (c) are repeated for different VH:VL pairs until an antibody with improved affinity is identified in step (c).

17. The method of claim 12 wherein three or more antibodies are obtained in step (a).

18. The method according to claim 12 further comprising the step (d) in which the antibody obtained in step (c) is humanised.

19. The method according to claim 12 in which the antibody obtained in step (c) of the method has an affinity of 100 pM or less.

20. The method according to claim 13 in which in step (b) each VH region from the antibodies obtained in step (a) is re-paired with each VL region such that every new VH:VL combination is produced as a recombinant antibody or fragment thereof and at least one of the recombinant antibodies produced is screened in step (c).

21. The method according to claim 13 in which steps (b) and (c) are repeated for different VH:VL pairs until an antibody with improved affinity is identified in step (c).

* * * * *